United States Patent
Bourque et al.

(10) Patent No.: US 10,028,800 B2
(45) Date of Patent: *Jul. 24, 2018

(54) RETROGRADE REAMER DEPTH TUBE GAGE

(71) Applicant: SMITH & NEPHEW, INC., Memphis, TN (US)

(72) Inventors: Bernard J. Bourque, Rehoboth, MA (US); David J. Callaghan, Waltham, MA (US)

(73) Assignee: Smith & Nephew, Inc., Memphis, TN (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/463,529

(22) Filed: Mar. 20, 2017

(65) Prior Publication Data

US 2017/0296288 A1    Oct. 19, 2017

Related U.S. Application Data

(63) Continuation of application No. 15/000,575, filed on Jan. 19, 2016, now Pat. No. 9,622,757, which is a (Continued)

(51) Int. Cl.
*A61B 90/00* (2016.01)
*A61B 17/16* (2006.01)
(Continued)

(52) U.S. Cl.
CPC .......... *A61B 90/06* (2016.02); *A61B 17/1615* (2013.01); *A61B 17/1633* (2013.01);
(Continued)

(58) Field of Classification Search
CPC ...... G01B 5/008; G01B 11/005; G01B 11/25; G01B 21/045; G01B 11/03; G01B 5/004;
(Continued)

(56) References Cited

U.S. PATENT DOCUMENTS 5,591,170 A    1/1997    Spievack
5,817,095 A    10/1998    Smith
(Continued)

FOREIGN PATENT DOCUMENTS

EP    1785103    5/2007
EP    2098177    9/2009
(Continued)

OTHER PUBLICATIONS

Office Action for EP App No. 13735099.7 dated Aug. 4, 2017, 6 pages.
(Continued)

*Primary Examiner* — Yaritza Guadalupe-McCall
(74) *Attorney, Agent, or Firm* — Joseph M. Maraia; Burns & Levinson, LLP

(57) ABSTRACT

A thickness gage including a transparent measurement tube configured to receive and be slidingly engaged over a tubular shaft of a retrograde reamer. The tubular shaft has linear graduation marks on its surface for identifying linear measures for use in measuring a thickness of a bridge bone gap. The linear graduation marks are located on the tubular shaft surface such that at least some of the linear graduation marks can be observed through the transparent measurement tube. Each linear graduation mark, when aligned with a proximal end of the measurement tube, provides a linear measure of the distance between a distal end of the measurement tube and a cutting member of the retrograde reamer positioned so that its central axis is disposed at a non-zero angle relative to a longitudinal axis of the tubular shaft. Such a distance corresponds to the thickness of the bridge bone gap.

15 Claims, 14 Drawing Sheets

Related U.S. Application Data continuation of application No. 14/290,003, filed on May 29, 2014, now Pat. No. 9,243,881.

(51) Int. Cl.
*A61B 17/17* (2006.01)
*A61B 17/00* (2006.01)

(52) U.S. Cl.
CPC ...... *A61B 17/1675* (2013.01); *A61B 17/1714* (2013.01); *A61B 2017/00902* (2013.01); *A61B 2090/062* (2016.02)

(58) Field of Classification Search
CPC ........ G01B 21/042; G01B 7/008; G01B 3/18; G01B 2003/1046
USPC .......................................... 33/451
See application file for complete search history.

(56) References Cited

U.S. PATENT DOCUMENTS

| | | | | |
|---|---|---|---|---|
| 6,024,746 | A * | 2/2000 | Katz | A61B 17/154 606/102 |
| 6,036,695 | A | 3/2000 | Smith | |
| 7,559,150 | B2 * | 7/2009 | Fernandez | A61B 5/103 33/512 |
| 7,607,238 | B2 * | 10/2009 | Kim | G01B 3/28 33/512 |
| 8,388,624 | B2 * | 3/2013 | Ek | A61B 17/1675 606/86 R |
| 8,888,781 | B2 * | 11/2014 | Sterrett | A61B 1/317 606/80 |
| 8,926,615 | B2 * | 1/2015 | Ek | A61B 17/1617 606/80 |
| 9,243,881 | B2 * | 1/2016 | Bourque | G01B 5/06 |
| 9,622,757 | B2 * | 4/2017 | Bourque | A61B 17/1633 |
| 2002/0032447 | A1 | 3/2002 | Weikel | |
| 2004/0199166 | A1 | 10/2004 | Schmieding | |
| 2004/0208717 | A1 | 10/2004 | Greenhalgh | |
| 2005/0240193 | A1 | 10/2005 | Reiley | |
| 2006/0207118 | A1 * | 9/2006 | Kim | A61B 5/1076 33/512 |
| 2007/0123921 | A1 | 5/2007 | Ek | |
| 2008/0114364 | A1 | 5/2008 | Goldin et al. | |
| 2008/0221505 | A1 | 9/2008 | Betts | |
| 2009/0171359 | A1 * | 7/2009 | Sterrett | A61B 1/317 606/80 |
| 2009/0228013 | A1 | 9/2009 | Bourque et al. | |
| 2010/0168750 | A1 | 7/2010 | Sherman | |
| 2011/0190832 | A1 | 8/2011 | Taylor et al. | |
| 2012/0130370 | A1 * | 5/2012 | Kinmon | A61B 17/7225 606/62 |
| 2012/0271357 | A1 | 10/2012 | Arthur et al. | |
| 2013/0184610 | A1 | 7/2013 | Bourque | |
| 2014/0276844 | A1 * | 9/2014 | Bourque | A61B 17/1714 606/80 |
| 2015/0038971 | A1 * | 2/2015 | Sterrett | A61B 1/317 606/80 |
| 2015/0345927 | A1 * | 12/2015 | Bourque | G01B 5/06 33/701 |
| 2016/0089162 | A1 * | 3/2016 | Ardito | A61B 17/1714 606/98 |
| 2016/0206329 | A1 * | 7/2016 | Bourque | G01B 5/06 |
| 2017/0296288 | A1 * | 10/2017 | Bourque | A61B 90/06 |

FOREIGN PATENT DOCUMENTS

| | | |
|---|---|---|
| JP | 2005152650 | 6/2005 |
| JP | 2008521511 | 6/2008 |
| JP | 4801225 B1 | 10/2011 |
| JP | 2012187384 | 10/2012 |

OTHER PUBLICATIONS

Office Action for JP App No. 2015-545818 dated Aug. 28, 2017, 7 pages.

* cited by examiner

RETROGRADE REAMER DEPTH TUBE GAGE

TECHNICAL FIELD

The present application relates generally to gages for use in performing ligament surgery, and more specifically to gages for measuring the depth of a tunnel or bore drilled through bone, as well as gages for measuring the thickness of bone.

BACKGROUND

While performing a ligament surgery procedure, it is often necessary for a surgeon to drill one or more tunnels or bores through a patient's bone. In such a ligament surgery procedure, the surgeon typically employs a surgical instrument to drill, in an antegrade fashion, a tunnel through the bone and into a space in the bone joint. Using the same surgical instrument or a different surgical instrument, the surgeon then typically deploys at least one cutter or blade of the surgical instrument within the bone joint space, and actuates the cutter or blade to drill, in a retrograde fashion, a counter bore through the bone along essentially the same path as the tunnel previously drilled in the antegrade fashion. In this way, a recipient socket can be formed in the patient's bone for placement and/or fixation of a tendon graft.

To assure proper formation of the recipient socket in the patient's bone, it is important for the surgeon to drill the counter bore through the bone to a desired depth. One known technique for measuring or otherwise gaging the depth of a tunnel or bore drilled through bone involves the use of a retrograde drill having a retrograde drill pin, and a drill depth grommet disposed or the retrograde drill pin. To obtain the desired depth of the tunnel or bore to be drilled through the bone, the surgeon can read markings on the retrograde drill pin relative to the patient's skin or bone surface before and during the formation of the recipient socket. However, such an approach for measuring or gaging the depth of a tunnel or bore drilled through bone can be difficult for a surgeon to perform, and can frequently produce loss than accurate measurement results.

SUMMARY

In accordance with the present application, a gage (also referred to herein as the "thickness gage") is provided for measuring or otherwise determining the thickness (also referred to herein as the "bridge bone gap") of bone remaining while drilling or after having drilled, in a retrograde fashion, a tunnel or bore through bone. The disclosed thickness gage is configured for use with a retrograde drill or reamer (also referred to herein as a/the "retrograde reamer"), which can include a tubular shaft, a drill bit disposed at a distal end of the tubular shaft, and at least one cutting member rotatably, slideably, or otherwise moveably disposed adjacent the distal end of the tubular shaft. The cutting member can be rotatably disposed adjacent the distal end of the tubular shaft such that it can rotate between a first position where its central axis is coincident with a longitudinal axis of the tubular shaft, and a second position where its central axis is disposed at a non-zero angle relative to the longitudinal axis of the tubular shaft.

In one aspect, the disclosed thickness gage includes a substantially transparent measurement tube configured to receive and be slidingly engaged over the tubular shaft of the retrograde reamer. In an exemplary aspect, the tubular shaft of the retrograde reamer has a plurality of linear graduation marks on its surface for identifying linear measures (e.g., 0 mm, 2 mm, 4 mm, 6 mm, 8 mm, . . . ) for use in measuring the thickness of the bridge bone gap. The linear graduation marks are located on the surface of the tubular shaft of the retrograde reamer such that at least some of the linear graduation marks can be observed through the substantially transparent measurement tube. Each of the linear graduation marks, when aligned with a proximal end of the measurement tube, provides at least an approximate linear measure of the distance between a distal end of the measurement tube and the cutting member of the retrograde reamer in its second position (i.e., where its central axis is disposed at a non-zero angle relative to the longitudinal axis of the tubular shaft of the retrograde reamer). Such a distance between the distal end of the measurement tuba and the cutting member in its second position corresponds to the thickness of the bridge bone gap.

In one mode of operating the disclosed thickness gage, a surgeon can establish, using a guide, a path for a guidewire at a surgical site through a patient's bone (e.g., a femur), place the guidewire along the established path, and then remove the guide. With the cutting member of the retrograde reamer in its first position (i.e., where its central axis is coincident with the longitudinal axis of the tubular shaft of the retrograde reamer), and the tubular shaft of the retrograde reamer placed over the guidewire, the surgeon can drill, in an antegrade fashion, a tunnel through the patient's femur and into a space in the femoral bone joint, using the drill bit at the distal end of the tubular shaft of the retrograde reamer. The surgeon can then at least partially retract the guidewire from the tubular shaft of the retrograde reamer to allow the cutting member to rotate, within the space in the femoral bone joint, from its first position to its second position (i.e., where its central axis is disposed at a non-zero angle relative to the longitudinal axis of the tubular shaft of the retrograde reamer). Next, the surgeon can advance the guidewire through the tubular shaft of the retrograde reamer, securing the cutting member in its angled second position.

Before drilling a counter bore through the patient's femur, the surgeon can position the measurement tube of the thickness gage over the tubular shaft of the retrograde reamer so that the distal end of the measurement tube makes contact against the surface of the femur. The surgeon can then drill, in a retrograde fashion, the counter bore through the femur along essentially the same path as the tunnel previously drilled in the antegrade fashion, with the retrograde reamer spinning freely independent of the thickness gage and the distal end of the measurement tube being held firmly against the femur surface.

While the surgeon drills the counter bore through the patient's femur, he or she can pull or otherwise move the retrograde reamer in a proximal direction, thereby causing the tubular shaft of the retrograde reamer to move in the proximal direction relative to the measurement tube. The surgeon can continue to drill the counter bore in such a manner until the tubular shaft of the retrograde reamer moves to an extent where the proximal end of the measurement tube is aligned with a linear graduation mark (located on the surface of the tubular shaft of the retrograde reamer) that identifies the linear measure of a desired thickness of the bridge bone gap. At this point, the surgeon can (a) substantially immediately stop the drilling of the counter bore, (b) retract the guidewire from the tubular shaft of the retrograde reamer to allow the cutting member to rotate from its second position (i.e., where its central axis is disposed at the non-zero angle relative to the longitudinal axis of the tubular shaft of the retrograde reamer), back to its first position (i.e., where its central axis is coincident with the longitudinal axis of the tubular shaft of the retrograde reamer), and (c) pull the distal end of the tubular shaft of the retrograde reamer through the remaining portion of the tunnel previously drilled through the femur in the antegrade fashion, thereby removing the retrograde reamer from the surgical site.

By providing such a thickness gage configured for use with a retrograde drill or reamer, the thickness of bone remaining while drilling or after having drilled, in a retrograde fashion, a tunnel or bore through bone can be determined with increased accuracy and ease of use.

Other features, functions, and aspects of the invention will be evident from the Detailed Description that fellows.

BRIEF DESCRIPTION OF THE DRAWINGS

The accompanying drawings, which are incorporated in and constitute a part of this specification. Illustrate one or more embodiments described herein and, together with the Detailed Description, explain these embodiments. In the drawings:

FIG. 1b is an exploded view of the depth gage of FIG. 1a;

DETAILED DESCRIPTION

A depth gage is disclosed herein for use in determining the depth of a tunnel or bore drilled, in a retrograde fashion, through bone. The disclosed depth gage is configured for use with a retrograde drill or reamer (also referred to herein as a/the "retrograde reamer"), which can include a tubular shaft, a drill bit disposed at a distal end of the tubular shaft, at least one cutting member rotatably, slideably, or otherwise moveably disposed adjacent the distal end of the tubular shaft, and a bushing located adjacent a proximal end of the tubular shaft. The cutting member can be rotatably disposed adjacent the distal end of the tubular shaft such that it can rotate between a first position where its central axis is coincident with a longitudinal axis of the tubular shaft, and a second position where its central axis is disposed at a non-zero angle relative to the longitudinal axis of the tubular shaft.

Figure 1A:
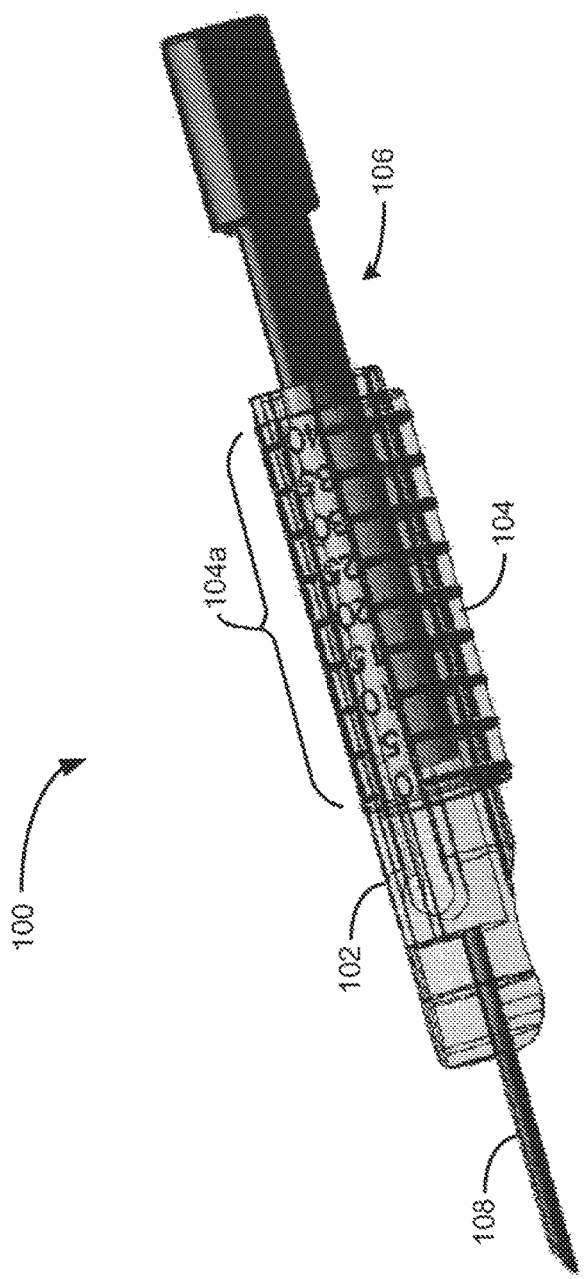
FIG. 1a is a perspective view of an exemplary depth gage for use in determining the depth of a tunnel or bore drilled, in a retrograde fashion, through bone, in accordance with the present application.
Figure 1B:
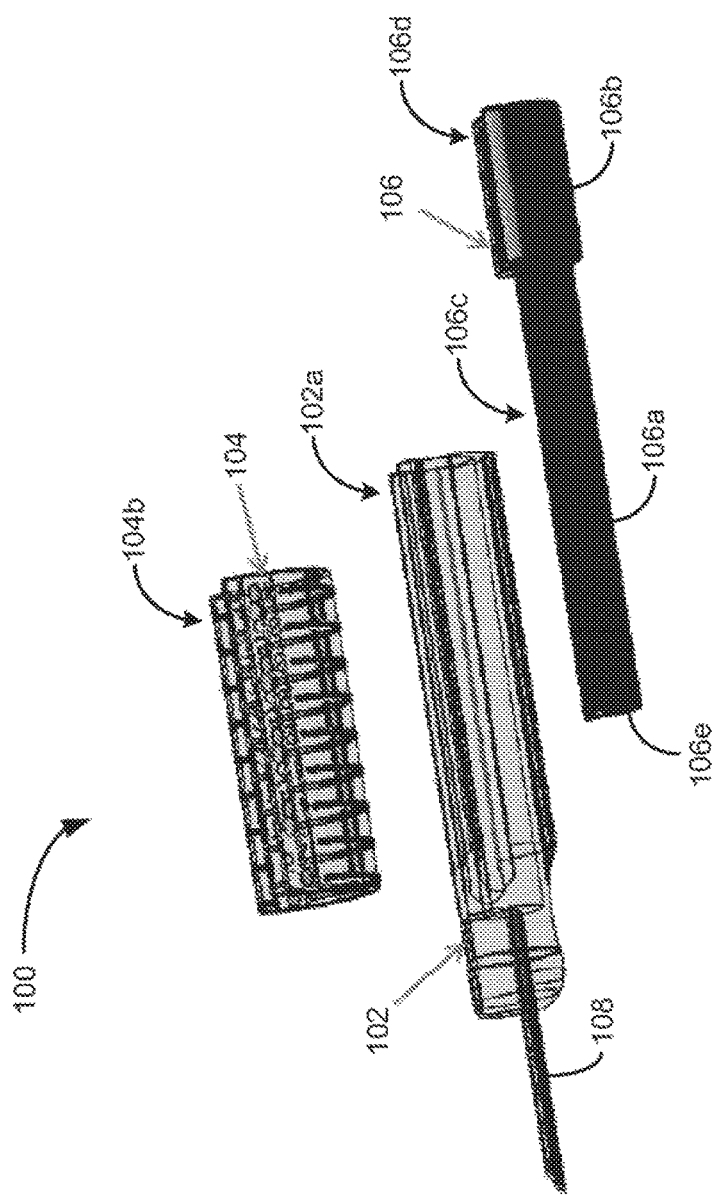

FIG. 1a depicts an illustrative embodiment of an exemplary depth gage 100 for use in determining the depth of a counter bore drilled, in a retrograde fashion, through bone, using a retrograde reamer, in accordance with the present application. FIG. 1b depicts an exploded view of the depth gage 100 of FIG. 1a. As shown in FIGS. 1a and 1b, the depth gage 100 includes a housing 102, a sliding ruler 104, a sliding reamer-docking element 106, and an elongated tip portion 108 attached at a distal end of the housing 102. The housing 102 and the sliding ruler 104 are each substantially tubular. The sliding reamer-decking element 108 has a substantially tubular section 106a (see FIG. 1b) at its distal end, as well as a portion 106b located at its proximal end that is configured to receive a bushing adjacent a proximal end of a tubular shaft of the retrograde reamer.

In an assembled form (see FIG. 1a), the housing 102 receives the tubular section 106a of the sliding reamer-docking element 106, and the sliding ruler 104 is slidingly engaged over the housing 102. The housing 102 and the sliding ruler 104 are each substantially transparent, while the sliding reamer-docking element 106 can be substantially opaque. The housing 102, the sliding ruler 104, and the sliding reamer-docking element 106 can each be made of injection-molded plastic, surgical grade plastic, or any other suitable material. For example, the housing 102 can be injection-molded onto the elongated tip portion 108. Further, the elongated tip portion 108 is substantially rigid, and can be made of stainless steel, surgical grade steel, or any other suitable material.

As shown in FIG. 1a, the sliding ruler 104 includes a plurality of linear graduation marks 104a for identifying linear measures (e.g., 0 mm, 5 mm, . . . , 35 mm, 40 mm) for use in measuring the depth of a counter bore drilled, in a retrograde fashion, through bone, using the retrograde reamer. The housing 102, the sliding ruler 104, and the tubular section 106a of the sliding reamer-docking element 106 each have a slot opening formed through and along their respective lengths. As shown in FIG. 1b, the housing 102 has a slot opening 102a, the sliding ruler 104 has a slot opening 104b, and the tubular section 106a of the sliding reamer-docking element 108 has a slot opening 106c. While the depth gage 100 is in its assembled form and the respective slot openings 102a, 104b, 106c are substantially in registration with one another, the depth gage 100 can be attached to the tubular shaft of the retrograde reamer by pressing the tubular shaft through the respective slot openings 102a, 104b, 106c to snappingly engage with at least the housing 102 and the tubular section 106a of the sliding reamer-docking element 106. The proximal portion 106b of the sliding reamer-docking element 106 likewise has a slot opening 106d formed through and along its length. As the tubular shaft of the retrograde reamer snappingly engages with the housing 102 and the tubular section 106a of the sliding reamer-docking element 106, the bushing of the retrograde reamer can be pressed through the slot opening 106d of the proximal portion 106b of the sliding reamer-docking element 106 to snappingly engage with the sliding reamer-docking element 106.

Figure 2A:
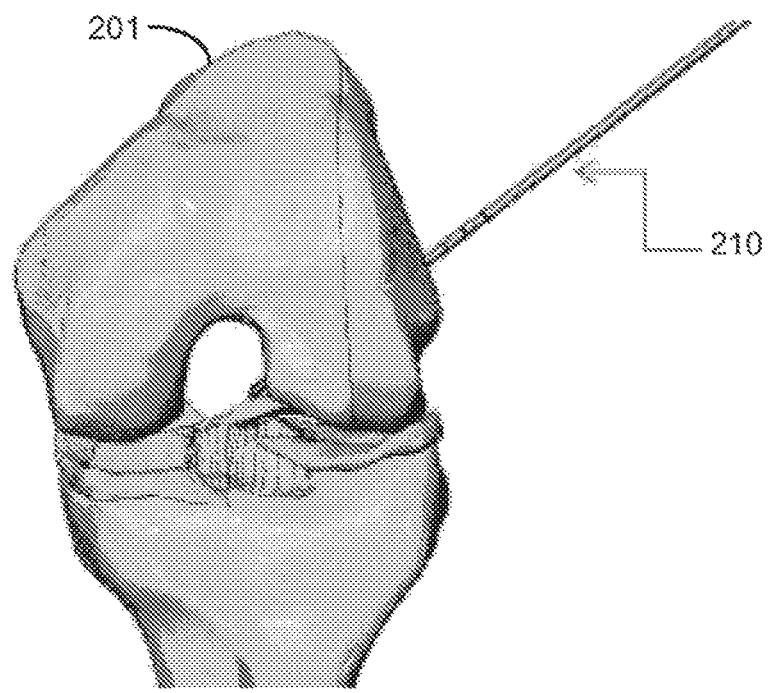
FIGS. 2a-2f illustrate an exemplary mode of operating the depth gage of FIGS. 1a and 1b, in conjunction with an exemplary retrograde reamer.
Figure 2B:
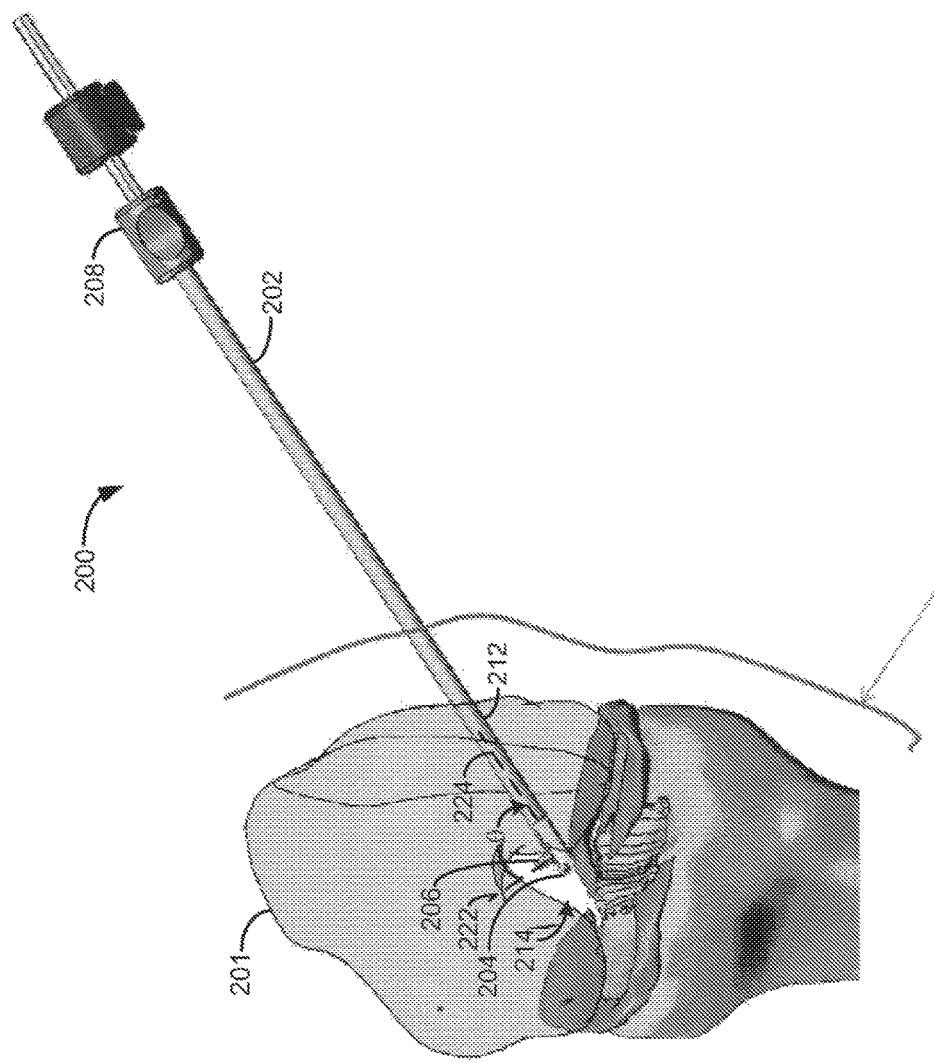
Figure 2C:
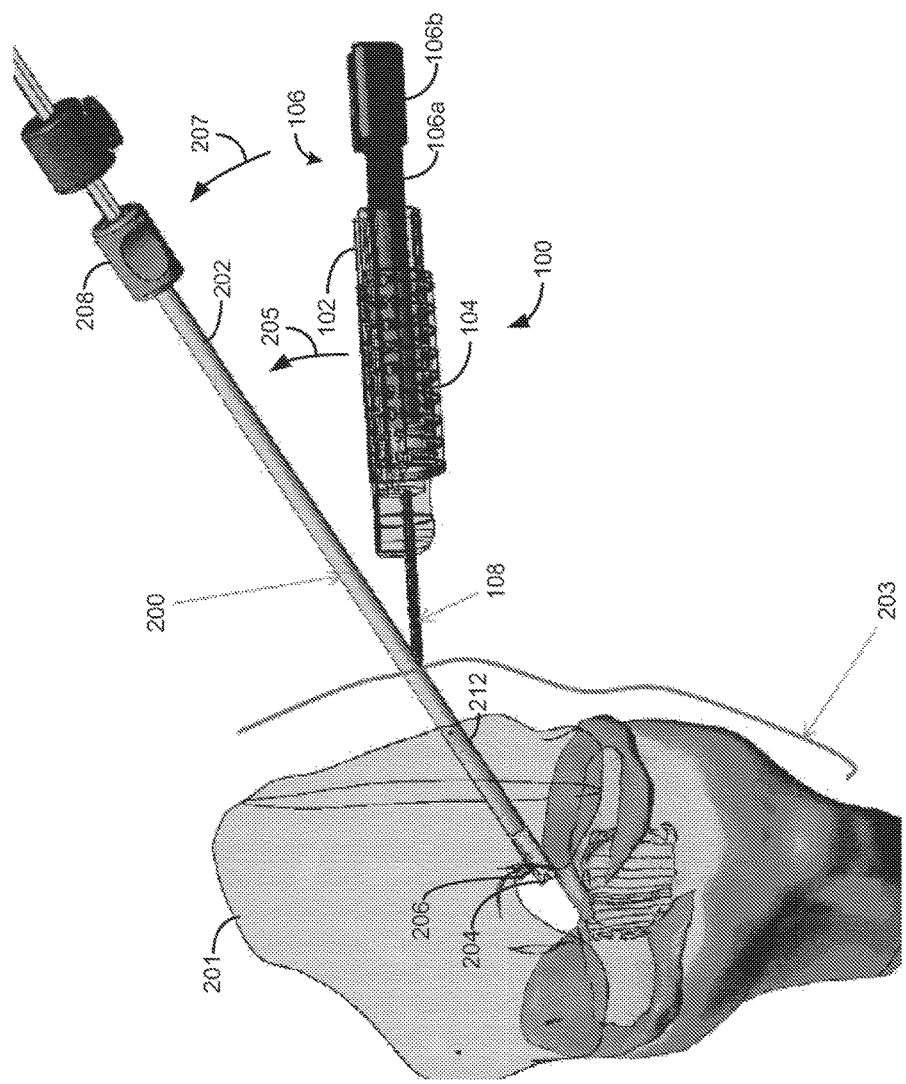

FIGS. 2a-2f illustrate an exemplary mode of operating the depth gage 100 of FIGS. 1a and 1b, in conjunction with an exemplary retrograde reamer 200 (see, e.g., FIG. 2b). As shown in FIG. 2b, the retrograde reamer 200 includes a tubular-shaft 202, a drill bit 204 disposed al a distal end of the tubular shaft 202, at least one cutting member 206 rotatably disposed adjacent the distal end of the tubular shaft 202, and a bushing 208 located adjacent a proximal end of the tubular shaft 202.

In this mode of operating the depth gage 100, a surgeon can establish, using a guide (not shown), a path for a guidewire 210 (see FIG. 2a) at a surgical site through a patient's bone (e.g., a femur 201; see FIG. 2a), place the guidewire 210 along the established path, and then remove the guide. With the outline member 206 of the retrograde reamer 200 in its first position (i.e., where its central axis 222 (see FIG. 2b) is coincident with a longitudinal axis 224 (see FIG. 2b) of the tubular shaft 200 of the retrograde reamer 200), and the tubular shaft 202 of the retrograde reamer 200 placed over the guidewire 210, the surgeon can drill, in an antegrade fashion (i.e., from the outside in), a tunnel 212 (see FIG. 2b) through the patient's femur 201 and into a space 214 (see FIG. 2b) in the femoral bone joint, using the drill bit 204 at the distal end of the tubular shaft 202. The surgeon can then at least partially retract the guidewire 210 from the tubular shaft 202 of the retrograde reamer 200 to allow the cutting member 206 to rotate, within the space 214 in the femoral bone joint, from its first position to its second position (i.e., where its central axis 222 is disposed at a non-zero angle θ (see, e.g., FIG. 2b) relative to the longitudinal axis 224 of the tubular shaft 202 of the retrograde reamer 200). Next, the surgeon can advance the guidewire 210 through the tubular shaft 202 of the retrograde reamer 200, securing the cutting member 206 in its angled second position.

Figure 2D:
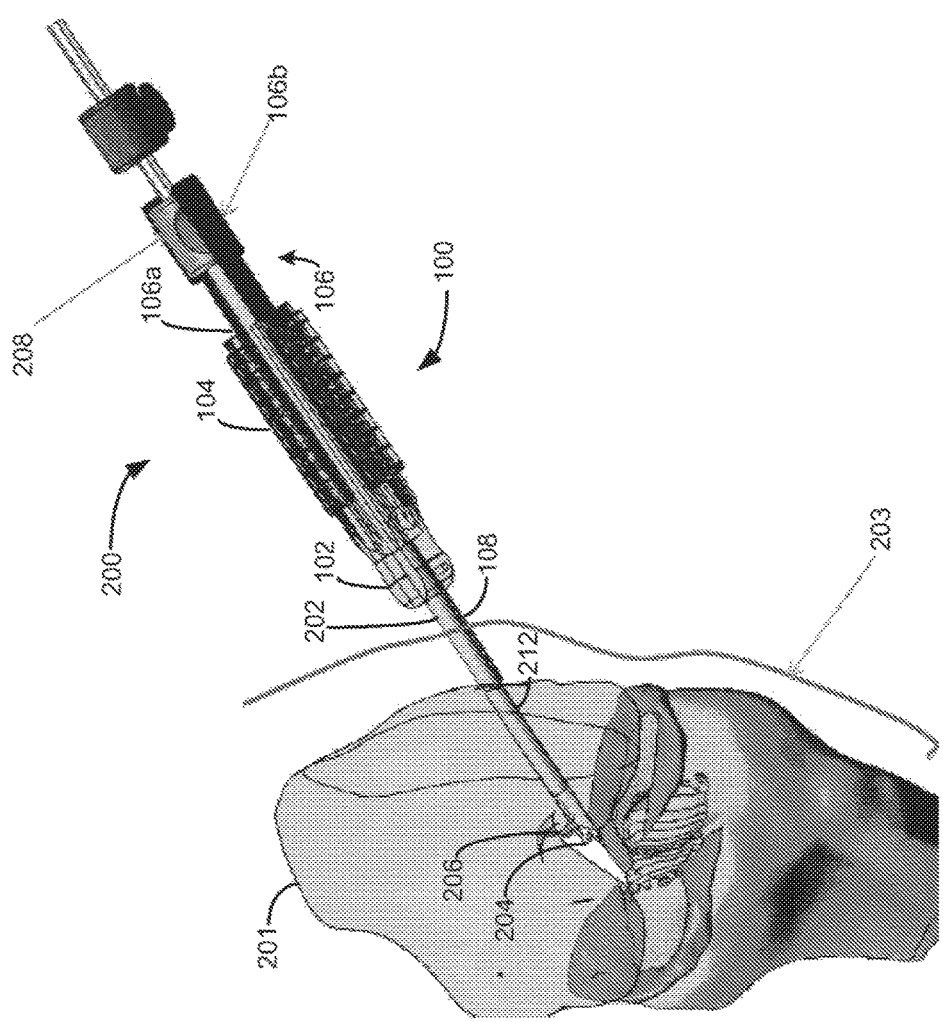
Figure 2E:
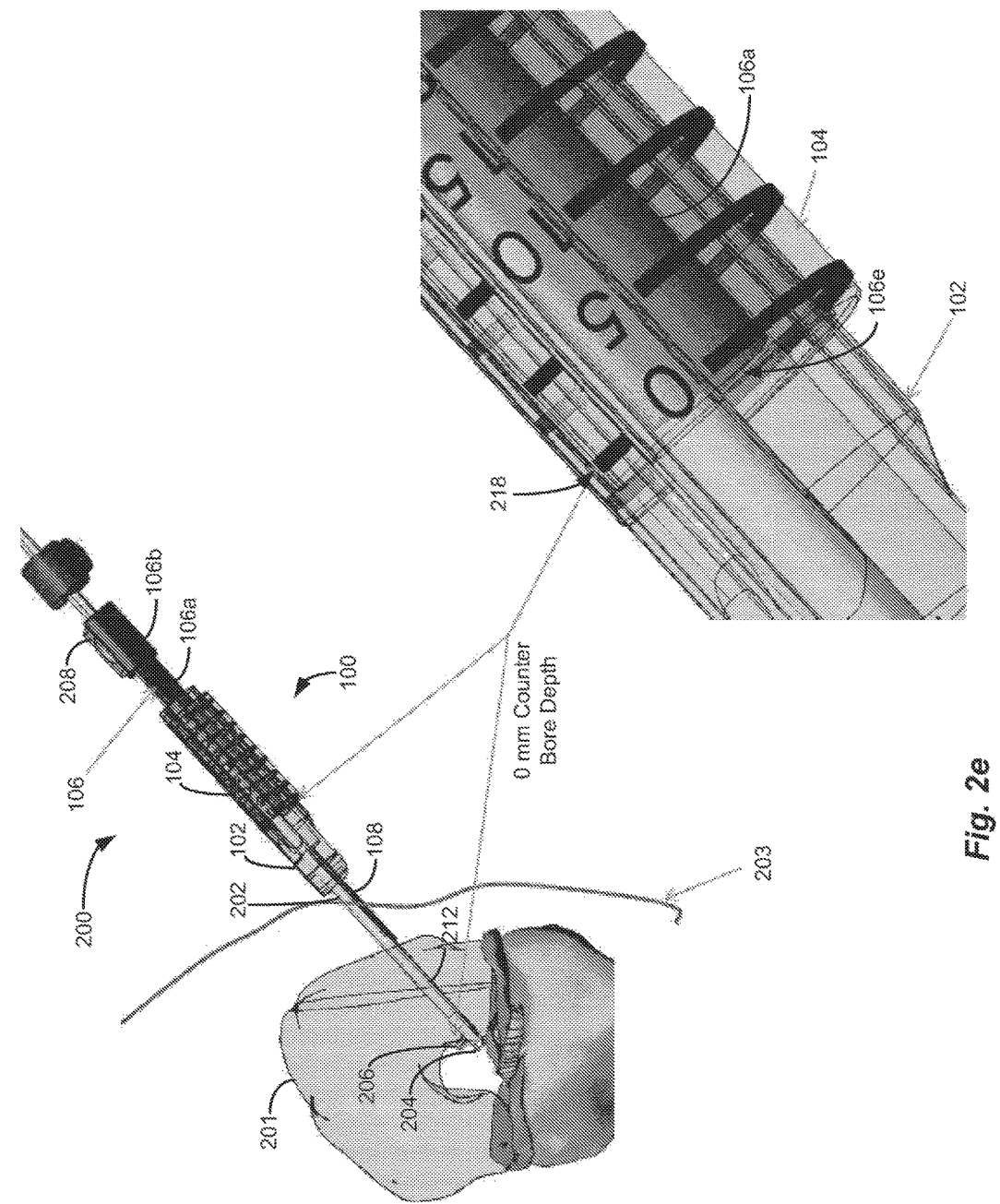
Figure 2F:
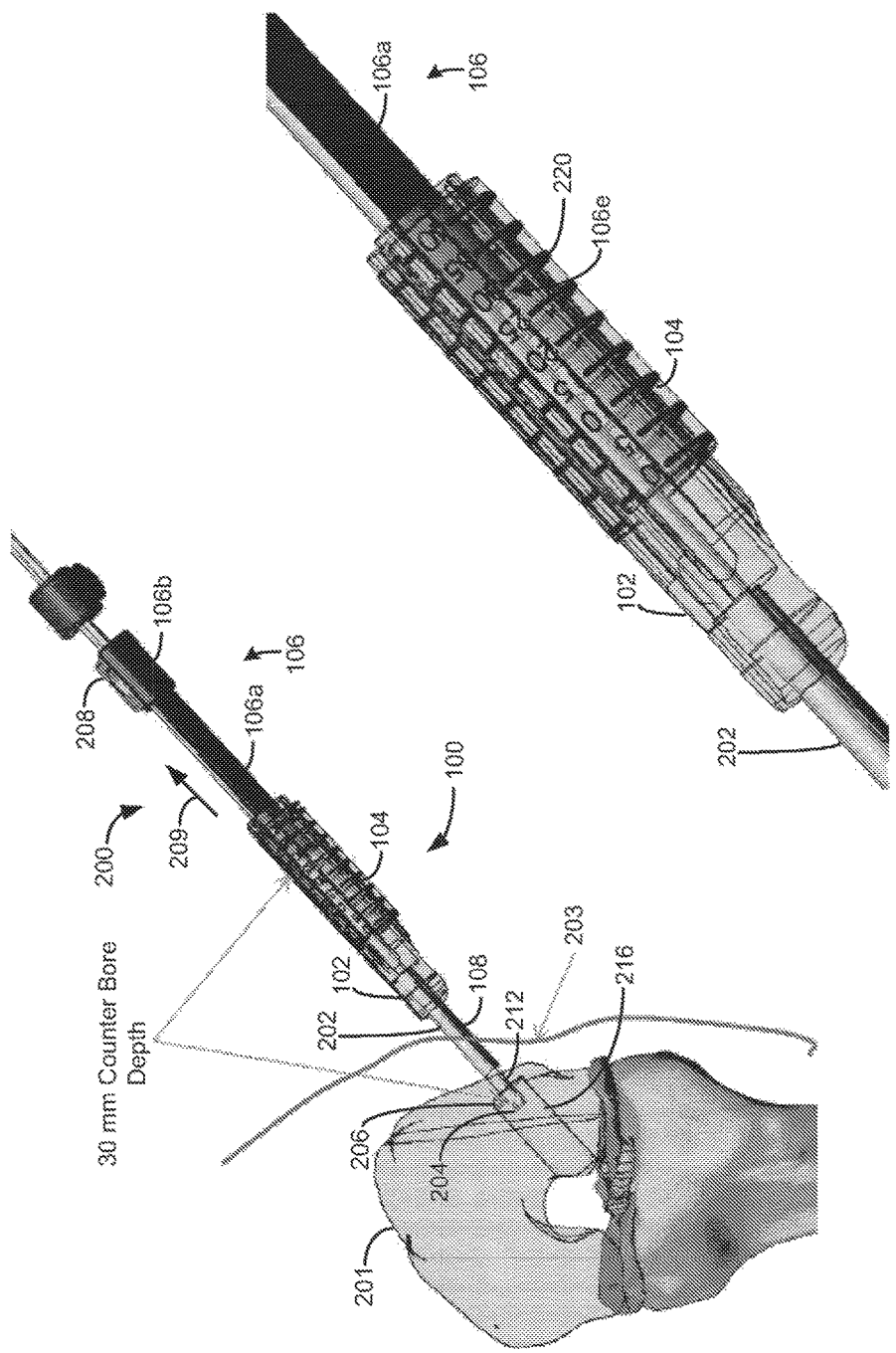

With the tubular shaft 202 of the retrograde reamer 200 placed over the guidewire 210 and the cutting member 206 in its second position, the surgeon can start to drill, in a retrograde fashion, a counter bore 216 (see FIG. 2f) through the femur 201 over the guidewire 210, using the cutting member 206 to drill along essentially the same path as the tunnel 212 previously drilled in the antegrade fashion. Once the cutting member 206 starts to drill the counter bore 216, the surgeon can (a) substantially immediately stop the drilling of the counter bore 216, (b) move the elongated tip portion 108 of the depth gage 100 along the tubular shaft 202 of the retrograde reamer 200 to a stable position against a surface of the patient's femur 201 or outer skin 203 (see FIG. 2c), (c) snappingly engage (in the direction of the directional arrow 205; see FIG. 2c) the tubular shaft 202 of the retrograde reamer 200 with the housing 102 and tubular section 106a of the sliding reamer-docking element 106 of the depth gage 100, and (d) snappingly engage (in the direction of the directional arrow 207; see FIG. 2c) the bushing 208 of the retrograde reamer 200 with the proximal portion 106b of the sliding reamer-docking element 106 of the depth gage 100. FIG. 2d depicts the depth gage 100 snappingly engaged with the retrograde reamer 200. As shown in FIG. 2d, the elongated tip portion 108 of the depth gage 100 is disposed along the tubular shaft 202 of the retrograde reamer 200 to a stable position against the surface of the patient's femur 201.

With the depth gage 100 snappingly engaged with the retrograde reamer 200, the surgeon can slide the sliding ruler 104 over and along the housing 102 (the housing 102 and the sliding ruler 104 each being substantially transparent) of the depth gage 100 to align the linear graduation mark (corresponding to reference numeral 218; see FIG. 2e) identifying the linear measure, 0 mm, with a distal end 106e (see FIGS. 1b and 2e) of the tubular section 106a of the sliding reamer-docking element 106. It is noted that the distal end 106e of the tubular section 106a of the sliding reamer-docking element 106, aligned with the linear graduation mark 218 identifying the linear measure, 0 mm, provides an indication that the current depth of the counter bore 216 is about 0 mm. The surgeon can then resume the drilling of the counter bore 216 through the patient's femur 201 with the retrograde reamer 200 spinning freely independent of the depth gage 100, while allowing the bushing 208 of the retrograde reamer 200 to pull the sliding reamer-docking element 106 in a proximal direction 209 (see FIG. 2f).

Such pulling of the sliding reamer-docking element 106 in the proximal direction 209 by the bushing 208 of the retrograde reamer 200 is allowed to continue until the distal end 106e of the tubular section 106a of the sliding reamer-docking element 106 is aligned with a linear graduation mark (e.g., a linear graduation mark 220; see FIG. 2f) of the sliding ruler 104 that identifies the linear measure corresponding to a desired depth of the counter bore 216, e.g., about 30 mm or any other suitable depth. At this point, the surgeon can (a) substantially immediately stop the drilling of the counter bore 216, (b) retract the guidewire 210 from the tubular shaft 202 of the retrograde reamer 200 to allow the cutting member 206 to rotate from its second position (i.e., where its central axis 222 is disposed at the non-zero angle θ relative to the longitudinal axis 224 of the tubular shaft 202 of the retrograde reamer 200), back to its first position (i.e., where its central axis 222 is coincident with the longitudinal axis 224 of the tubular shaft 202 of the retrograde reamer 200), and (a) pull the distal end of the tubular shaft 202 of the retrograde reamer 200 through the remaining portion of the tunnel 212 previously drilled through the femur 201 in the antegrade fashion, thereby removing the retrograde reamer 200 from the surgical site.

Figure 3:
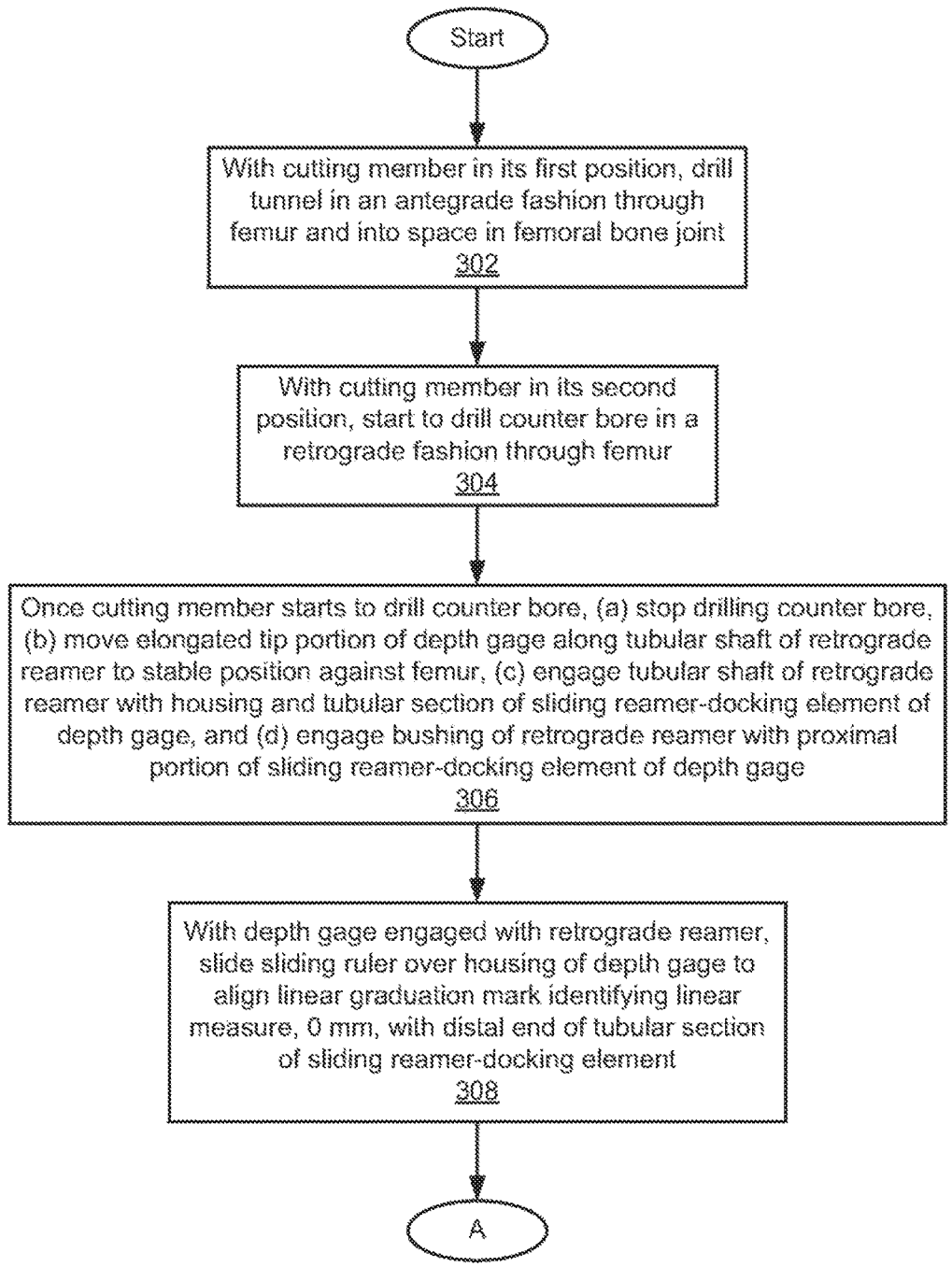
FIG. 3 is a flow diagram of an exemplary method of operating the depth gage of FIGS. 1a and 1b.
Figure 3:
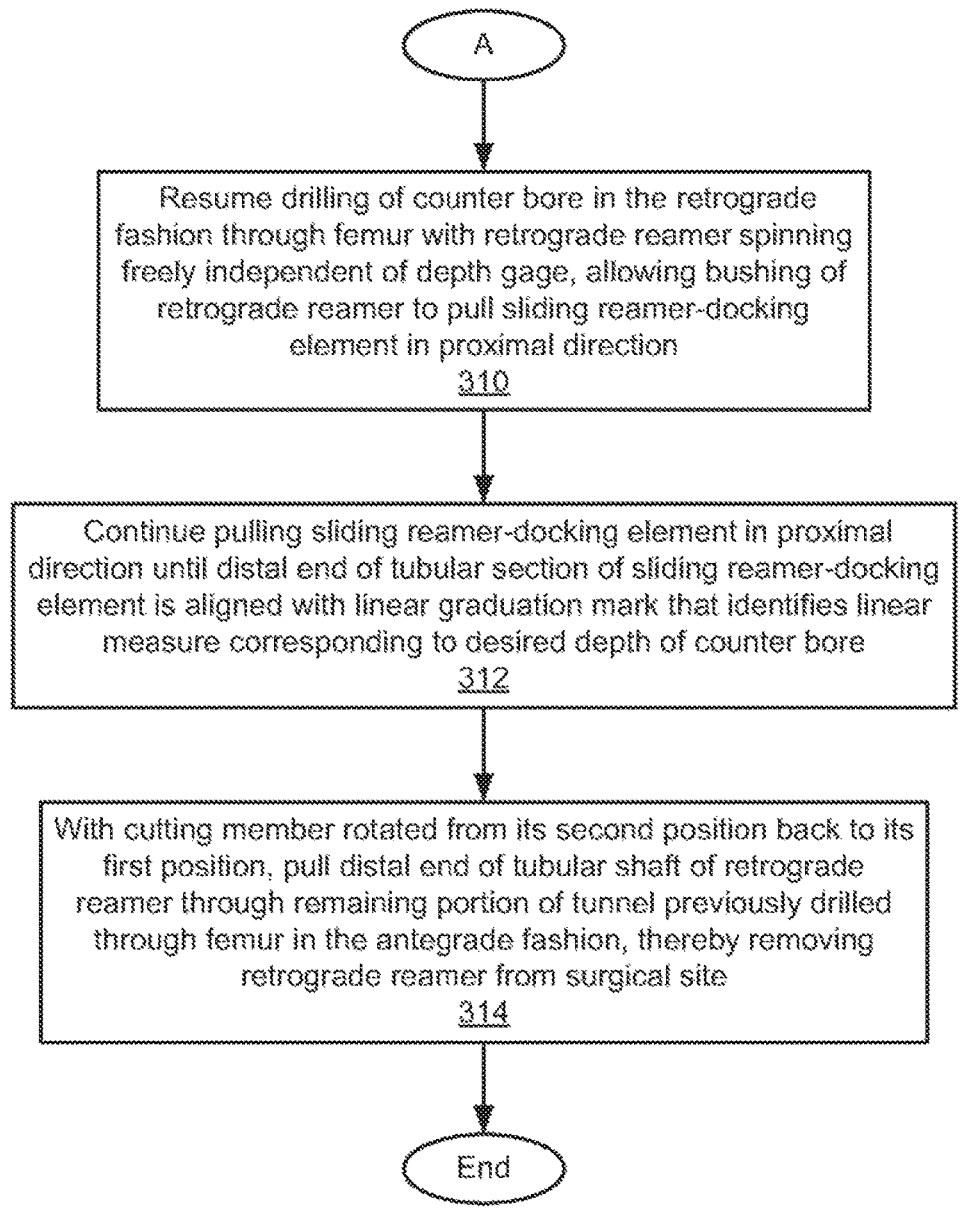

An exemplary method of operating the depth gage 100 is described below with reference to FIG. 3, as well as FIGS. 1a, 1b, and 2a-2f. As depicted in block 302 (see FIG. 3), with the cutting member 206 of the retrograde reamer 200 in its first position (i.e., where its central axis 222 is coincident with the longitudinal axis 224 of the tubular shaft 202), the tunnel 212 is drilled, in an antegrade fashion, through the patient's femur 201 and into the space 214 in the femoral bone joint, using the drill bit 204 at the distal end of the tubular shaft 202. As depicted in block 304, with the cutting member 206 in its second position (i.e., where its central axis 222 is disposed at the non-zero angle θ relative to the longitudinal axis 224 of the tubular shaft 202), the counter bore 216 is started to be drilled, in a retrograde fashion, through the femur 201, using the cutting member 206 to drill along essentially the same path as the tunnel 212 previously drilled in the antegrade fashion.

As depicted in block 306, once the cutting member 206 starts to drill the counter bore 216, (a) the drilling of the counter bore 216 is stopped, (b) the elongated tip portion 108 of the depth gage 100 is moved along the tubular shaft 202 of the retrograde reamer 200 to a stable position against the surface of the patient's femur 201 or outer skin 203, (c) the tubular shaft 202 of the retrograde reamer 200 is snappingly engaged with the housing 102 and tubular section 106a of the sliding reamer-docking element 106 of the depth gage 100, and (d) the bushing 208 of the retrograde reamer 200 is snappingly engaged with the proximal portion 106b of the sliding reamer-docking element 106 of the depth gage 100.

As depicted in block 308, with the depth gage 100 snappingly engaged with the retrograde reamer 200, the sliding ruler 104 is slid over and along the housing 102 of the depth gage 100 to align the linear graduation mark 218 identifying the linear measure, 0 mm, with the distal end 106e of the tubular section 106a of the sliding reamer-docking element 106. As depicted in block 310, the drilling of the counter bore 216 through the patient's femur 201 is resumed with the retrograde reamer 200 spinning freely independent of the depth gage 100, while allowing the bushing 208 of the retrograde reamer 200 to pull the sliding reamer-docking element 106 in the proximal direction 209.

As depicted in block 312, such pulling of the sliding reamer-docking element 106 by the bushing 208 of the retrograde reamer 200 is continued until the distal end 106e of the tubular section 106a of the sliding reamer-docking element 106 is aligned with the linear graduation mark 220 that identifies the linear measure corresponding to a desired depth of the counter bore 212, e.g., about 30 mm or any other suitable depth. As depicted in block 314, with the cutting member 206 of the retrograde reamer 200 rotated from its second position (i.e., where its central axis 222 is disposed at the non-zero angle θ relative to the longitudinal axis 224 of the tubular shaft 202) back to its first position (i.e., where its central axis 222 is coincident with the longitudinal axis 224 of the tubular shaft 202), the distal end of the tubular shaft 202 of the retrograde reamer 200 is pulled through the remaining portion of the tunnel 212 previously drilled through the femur 201 in the antegrade fashion, thereby removing the retrograde reamer 200 from the surgical site.

Having described the above exemplary embodiments of the disclosed depth gage, other alternative embodiments or variations may be made. For example, FIG. 4 depicts an illustrative embodiment of an exemplary thickness gage 400 for measuring or otherwise determining the thickness (also referred to herein as the "bridge bone gap") of bone remaining while drilling or after having drilled, in a retrograde fashion, a counter bore (such as the counter bore 216) through bone (such as the femur 201) using a retrograde reamer (such as the retrograde reamer 200), in further accordance with the present application.

Figure 4:
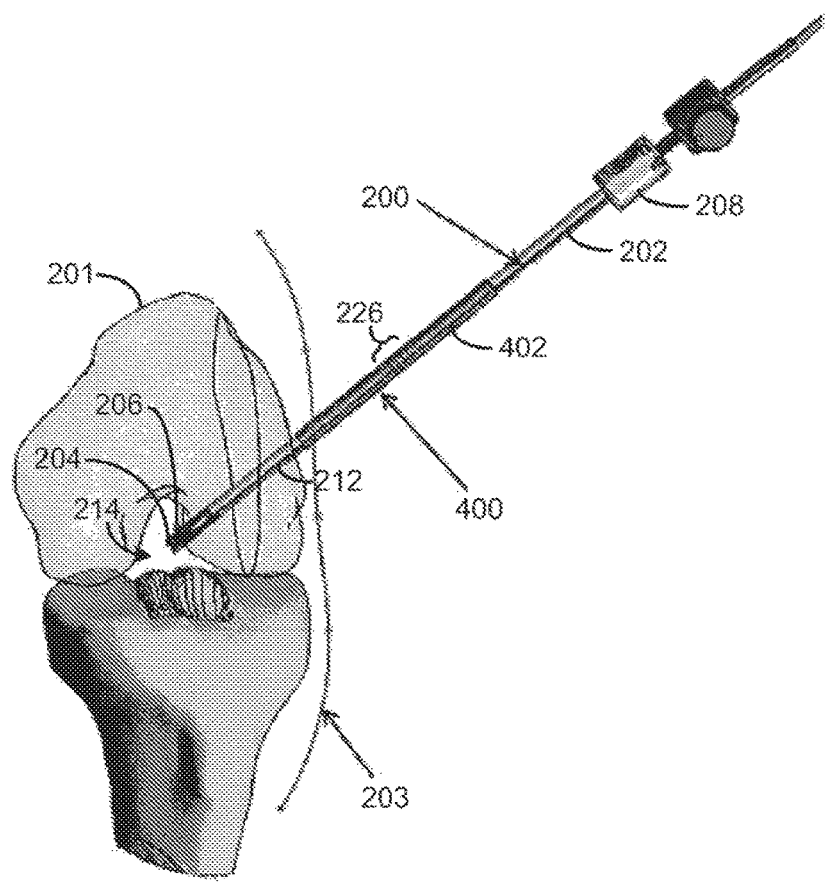
FIG. 4 is a perspective view of an exemplary thickness gage for use in determining the thickness of bone remaining while drilling or after having drilled, in a retrograde fashion, a tunnel or bore through bone using an exemplary retrograde reamer, in further accordance with the present application.

As shown in FIG. 4, the thickness gage 400 includes a substantially transparent measurement tube 402 configured to receive and be slidingly engaged over the tubular shaft 202 of the retrograde reamer 200. For example, the measurement tube 402 can be made of plastic, surgical grade plastic, or any other suitable material. The tubular shaft 202 of the retrograde reamer 200 has a plurality of linear graduation marks (including exemplary linear graduation marks 226; see FIGS. 4 and 5c) on its surface for identifying linear measures (e.g., . . . 4 mm, 6 mm, 8 mm, 10 mm . . . ; see FIG. 5c) for use in measuring the thickness of the bridge bone gap. The linear graduation marks 226 are located on the surface of the tubular shaft 202 of the retrograde reamer 200 such that at least some of the linear graduation marks 226 can be observed through the substantially transparent measurement tube 402, as illustrated in FIG. 4. Each of the linear graduation marks 226, when aligned with a proximal end 404 (see FIGS. 5b and 5c) of the measurement tube 402, provides at least an approximate linear measure of the distance between a distal end 406 (see FIGS. 5b and 5c) of the measurement tube 402 and the cutting member 206 of the retrograde reamer 200 in its second position (i.e., where the central axis 222 of the cutting member 206 is disposed at a non-zero angle relative to the longitudinal axis 224 of the tubular shaft 202). Such a distance between the distal end 406 of the measurement tube 402 and the cutting member 206 in its second position corresponds to the thickness of the bridge bone gap (such as a bridge bone gap 410; see FIG. 5c).

It is noted that, in the event the measurement tube 402, disposed over the tubular shaft 202 of the retrograde reamer 200, were to make contact against the cutting member 206 in its second position (i.e., where the central axis 222 of the cutting member 206 is disposed at a non-zero angle-relative to the longitudinal axis 224 of the tubular shaft 202) during use, a linear graduation mark identifying the linear measure, 0 mm, would preferably be aligned with the proximal end 404 of the measurement tube 402, thereby indicating that the resulting thickness of the bridge bone gap is about 0 mm.

Figure 5A:
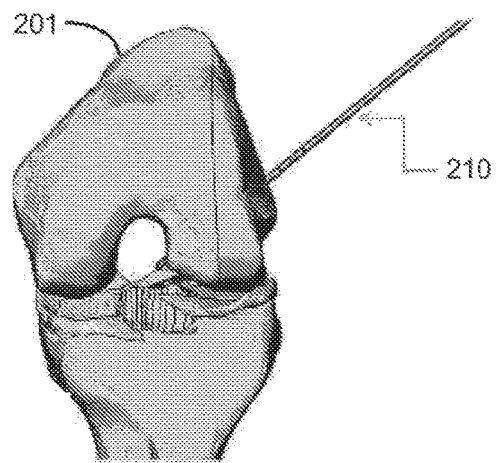
FIGS. 5a-5c illustrate an exemplary mode of operating the thickness gage of FIG. 4, in conjunction with the retrograde reamer of FIG. 4.
Figure 5B:
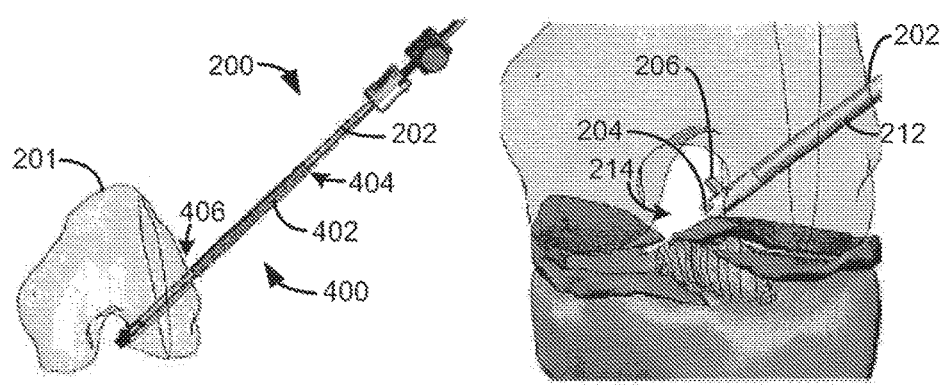
Figure 5C:
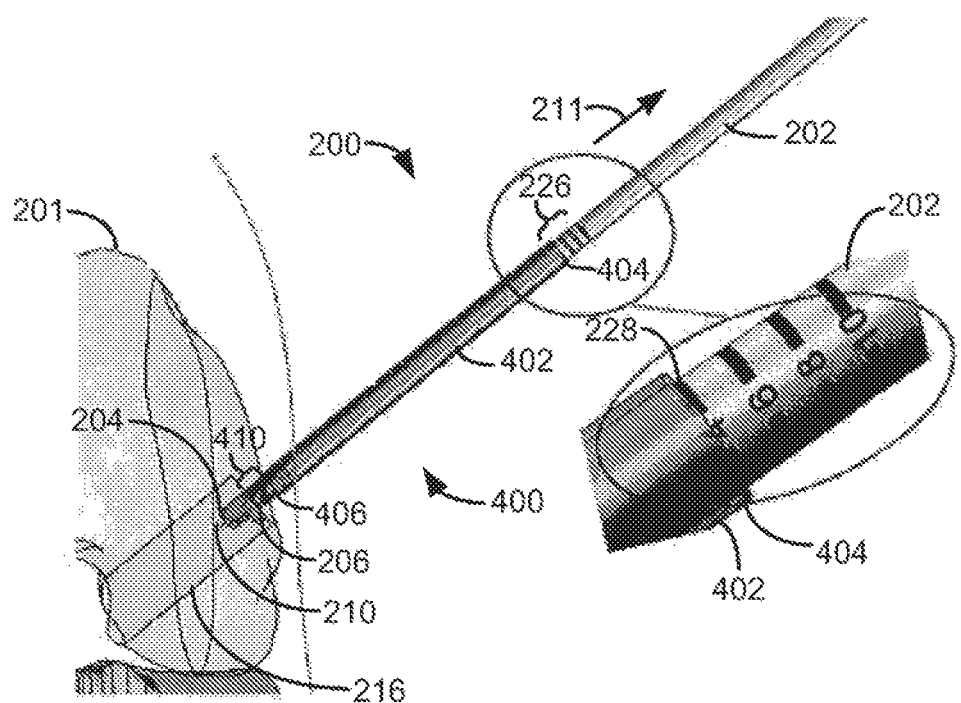

FIGS. 5a-5c illustrate an exemplary mode of operating the thickness gage 400 of FIG. 4, in conjunction with the retrograde reamer 200. In this mode of operating the thickness gage 400, a surgeon can establish, using a guide (not shown), a path for the guidewire 210 (see FIG. 5a) at a surgical site through a patient's bone (e.g., the femur 201), place the guidewire 210 along the established path, and then remove the guide. With the cutting member 206 of the retrograde reamer 200 in its first position (i.e., where its central axis 222 is coincident with the longitudinal axis 224 of the tubular shaft 202), and the tubular shaft 202 of the retrograde reamer 200 placed over the guidewire 210, the surgeon can drill, in an antegrade fashion, a tunnel (such as the tunnel 212; see FIG. 5b) through the patient's femur 201 and into the space 214 in the femoral bone joint, using the drill bit 204 at the distal end of the tubular shaft 202. The surgeon can than at least partially retract the guidewire 210 from the tubular shaft 202 of the retrograde reamer 200 to allow the cutting member 206 to rotate, within the space 214 in the femoral bone joint, from its first position to its second position (i.e., where its central axis 222 is disposed at a non-zero angle relative to the longitudinal axis 224 of the tubular shaft 202). Next, the surgeon can advance the guidewire 210 through the tubular shaft 202 of the retrograde reamer 200, securing the cutting member 206 in its angled second position.

Before drilling a counter bore (such as the counter bore 216) through the femur 201, the surgeon positions the measurement tube 402 of the thickness gage 400 over the tubular shaft 202 of the retrograde reamer 200 so that the distal end 406 of the measurement tube 402 makes contact against the surface of the femur 201, as illustrated in FIG. 5c. The surgeon then drills the counter bore 216 (see FIG. 5c), in a retrograde fashion, through the femur 201 along essentially the same path as the tunnel 212 previously drilled in the antegrade fashion, with the retrograde reamer 200 spinning freely independent of the thickness gage 400 and the distal end 406 of the measurement tube 402 being held firmly against the femur surface.

While the surgeon drills the counter bore 216 through the patient's femur 201, he or she can pull or otherwise move the retrograde reamer 200 in a proximal direction 211 (see FIG. 5c), thereby causing the tubular shaft 202 of the retrograde reamer 200 to move in the proximal direction 211 relative to the measurement tube 402. The surgeon can continue to drill the counter bore 216 in such a manner until the tubular shaft 202 of the retrograde reamer 200 moves to an extent where the proximal end 404 of the measurement tube 402 is aligned with a linear graduation mark (e.g., a linear graduation mark 228; see FIG. 5c) that identifies the linear measure of a desired thickness of the bridge bone gap 410, e.g., about 4 mm or any other suitable thickness. At this point the surgeon can (a) substantially immediately stop the drilling of the counter bore 216, (b) retract the guidewire 210 from the tubular shaft 202 of the retrograde reamer 200 to allow the cutting member 206 to rotate from its second position (i.e., where its central axis 222 is disposed at the non-zero angle relative to the longitudinal axis 224 of the tubular shaft 202) back to its first position (i.e., where its central axis 222 is coincident with the longitudinal axis 224 of the tubular shaft 202), and (c) pull the distal end of the tubular shaft 202 of the retrograde reamer 200 through the remaining portion of the tunnel 212 previously drilled through the femur 201 in the antegrade fashion, thereby removing the retrograde reamer 200 from the surgical site.

Figure 6:
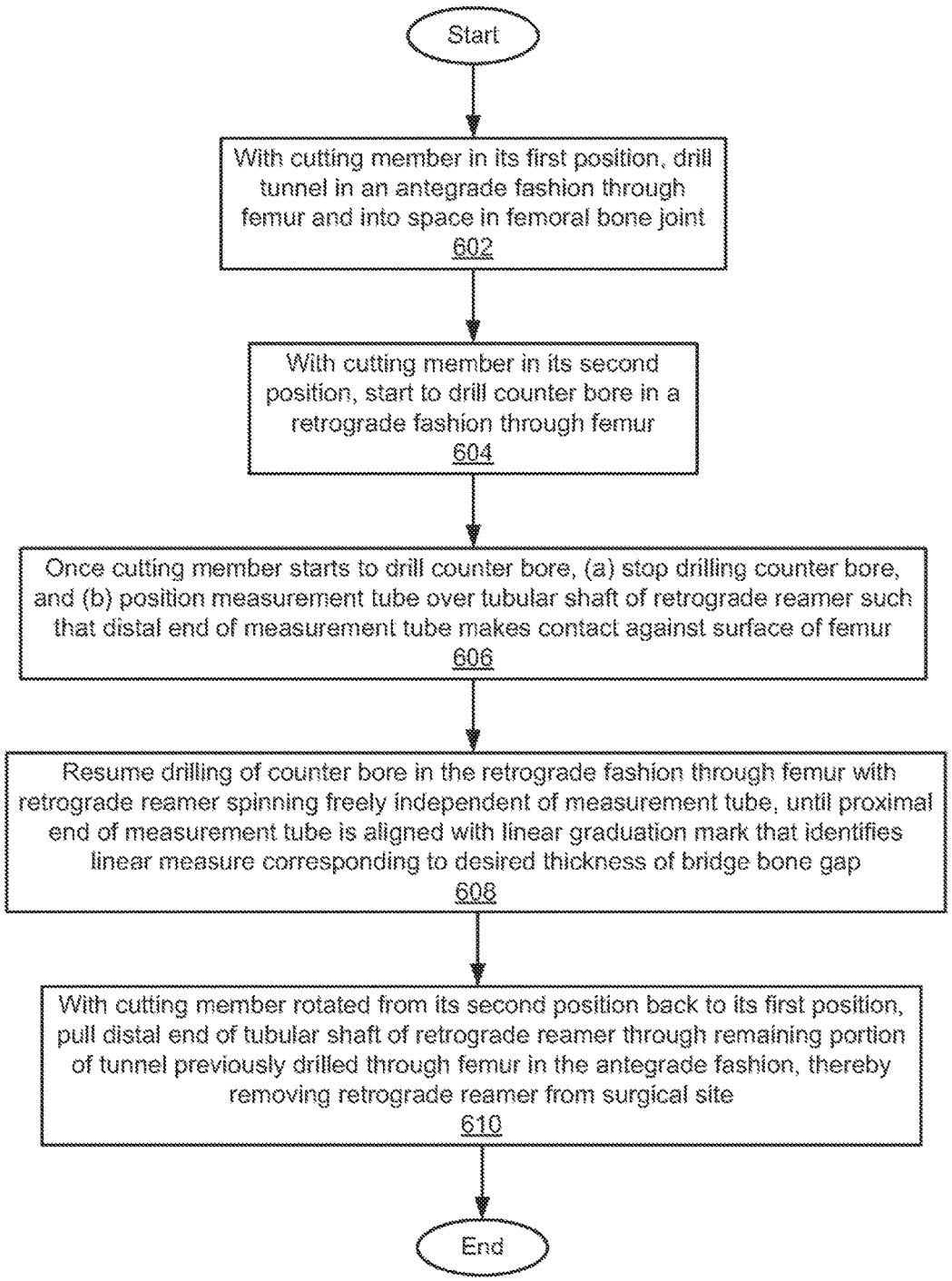
FIG. 6 is a flow diagram of an exemplary method of operating the thickness gage of FIG. 4.

An exemplary method of operating the thickness gage 400 is described below with reference to FIG. 6, as well as FIGS.

4 and 5a-5c. As depicted in block 602 (see FIG. 6), with the cutting member 206 of the retrograde reamer 200 in its first position (i.e., where its central axis 222 is coincident with the longitudinal axis 224 of the tubular shaft 202), the tunnel 212 is drilled, in an antegrade fashion at a surgical site, through the femur 201 and into the space 214 in the femoral bone joint. As depicted in block 604, with the cutting member 206 of the retrograde reamer 200 in its second position (i.e., where its central axis 222 is disposed at a non-zero angle relative to the longitudinal axis 224 of the tubular shaft 202), the counter bore 216 is started to be drilled, in a retrograde fashion, through the femur 201. As depicted in block 606, once the cutting member 206 starts to drill the counter bore 216, (a) the drilling of the counter bore 216 is stopped, and (b) the measurement tube 402 is positioned over the tubular shaft 202 of the retrograde reamer 200 so that the distal end 406 of the measurement tube 402 makes contact against the surface of the femur 201. Alternatively, the measurement tube 402 can be positioned over the tubular shaft 202 of the retrograde reamer 200 (so that the distal end 406 of the measurement tube 402 makes contact against the surface of the femur 201) before the drilling of the counter bore 216 is started.

As depicted in block 608, the drilling of the counter bore 216, in the retrograde fashion, through the femur 201 is resumed, with the retrograde reamer 200 spinning freely independent of the measurement tube 402, until the proximal end 404 of the measurement tube 402 is aligned with a linear graduation mark that identifies the linear measure corresponding to a desired thickness of the budge bone gap, such as 4 mm or any other suitable thickness. As depleted in block 610, with the cutting member 206 rotated from its second position (i.e., where its central axis 222 is disposed at the non-zero angle relative to the longitudinal axis 224 of the tubular shaft 202) back to its first position (i.e., where its central axis 222 is coincident with the longitudinal axis 224 of the tubular shaft 202), the distal end of the tubular shaft 202 of the retrograde reamer 200 is pulled through the remaining portion of the tunnel 212 previously drilled through the femur 201 in the antegrade fashion, thereby removing the retrograde reamer 200 from the surgical site.

It will be appreciated by those of ordinary skill in the art that further modifications to and variations of the above-described depth and thickness gages may be made without departing from the inventive concepts disclosed herein. Accordingly, the invention should not be viewed as limited except as by the scope and spirit of the appended claims.

What is claimed is:

1. A device for measuring a thickness of target material, the device being configured for use in conjunction with a retrograde drill including a tubular shaft, a drill bit disposed at a distal end of the tubular shaft, and at least one cutting member moveably disposed adjacent the distal end of the tubular shaft, the device comprising:
   a substantially transparent measurement tube having a proximal end and a distal end, the measurement tube being configured to receive and be slidingly engaged over the tubular shaft of the retrograde drill,
   wherein the cutting member of the retrograde drill is operative to move between a first position where a central axis thereof is coincident with a longitudinal axis of the tubular shaft of the retrograde drill, and a second position where the central axis thereof is disposed at a non-zero angle relative to the longitudinal axis of the tubular shaft of the retrograde drill,
   wherein the tubular shaft of the retrograde drill has a plurality of linear graduation marks on a surface thereof for identifying a plurality of linear measures, respectively, at least some of the plurality of linear graduation marks being observable through the substantially transparent measurement tube, and
   wherein each of the plurality of linear graduation marks aligned with the proximal end of the measurement tube provides a respective linear measure of a distance between the distal end of the measurement tube and the cutting member of the retrograde drill disposed in the second position, the respective linear measure corresponding to the thickness of the target material remaining while drilling or after having drilled a tunnel or bore through the target material using the retrograde drill.

2. The device of claim 1 wherein the measurement tube is substantially rigid.

3. The device of claim 1 wherein the measurement tube is made of a material selected from the group consisting of plastic and surgical grade plastic.

4. The device of claim 1 wherein the target material is bone, and wherein the measurement tube is operative to measure, in a ligament surgery procedure, the thickness of the bone remaining while drilling or after having drilled the tunnel or bore through the bone using the retrograde drill.

5. A system for measuring a thickness of target material comprising:
   a retrograde drill including a tubular shaft having a surface, a distal end, and a longitudinal axis, a drill bit disposed at the distal end of the tubular shaft, and at least one cutting member having a central axis, the cutting member being moveably disposed adjacent the distal end of the tubular shaft; and
   a substantially transparent measurement tube having a proximal end and a distal end, the measurement tube being configured to receive and be slidingly engaged over the tubular shaft of the retrograde drill,
   wherein the cutting member is operative to move between a first position where the central axis thereof is coincident with the longitudinal axis of the tubular shaft and a second position where the central axis thereof is disposed at a non-zero angle relative to the longitudinal axis of the tubular shaft, the retrograde drill being operative to drill, in a retrograde fashion, at least one tunnel or bore through the target material with the cutting member of the retrograde drill disposed in the second position,
   wherein the tubular shaft of the retrograde drill has a plurality of linear graduation marks on the surface thereof for identifying a plurality of linear measures, respectively, at least some of the plurality of linear graduation marks being observable through the substantially transparent measurement tube, and
   wherein each of the plurality of linear graduation marks aligned with the proximal end of the measurement tube provides a respective linear measure of a distance between the distal end of the measurement tube and the cutting member of the retrograde drill disposed in the second position, the respective linear measure corresponding to the thickness of the target material remaining while drilling or after having drilled, in the retrograde fashion, the at least one tunnel or bore through the target material.

6. The system of claim 5 wherein the measurement tube is substantially rigid.

7. The system of claim 5 wherein the measurement tube is made of a material selected from the group consisting of plastic and surgical grade plastic.

8. The system of claim 5 wherein the retrograde drill is further operative to drill, in an antegrade fashion using the drill bit, at least another tunnel or bore through the target material with the cutting member of retrograde drill disposed in the first position.

9. The system of claim 8 wherein the retrograde drill is further operative to drill, in the retrograde fashion, the at least one tunnel or bore through the target material, and to drill, in the antegrade fashion, the at least another tunnel or bore through the target material, along substantially the same path through the target material.

10. The system of claim 5 wherein the retrograde drill is further operative, while drilling the at least one tunnel or bore, to spin freely independent of the measurement tube.

11. The system of claim 5 wherein the target material is bone, and wherein the measurement tube is operative to measure, in a ligament surgery procedure, the thickness of the bone remaining while drilling or after having drilled the at least one tunnel or bore through the bone using the retrograde drill.

12. A method of measuring a thickness of target material, comprising:
   providing a retrograde drill including a tubular shaft having a surface, a distal end, and a longitudinal axis, a drill bit disposed at the distal end of the tubular shaft, and at least one cutting member having a central axis, the cutting member being moveably disposed adjacent the distal end of the tubular shaft;
   providing a substantially transparent measurement tube having a proximal end and a distal end, the measurement tube being configured to receive and be slidingly engaged over the tubular shaft of the retrograde drill;
   moving the culling member of the retrograde drill from a first position where the central axis thereof is coincident with the longitudinal axis of the tubular shaft, to a second position where the central axis thereof is disposed at a non-zero angle relative to the longitudinal axis of the tubular shaft;
   drilling, in a retrograde fashion by the retrograde drill, at least one tunnel or bore through the target material with the cutting member of the retrograde drill disposed in the second position, the tubular shaft of the retrograde drill having a plurality of linear graduation marks on the surface thereof for identifying a plurality of linear measures, respectively, at least some of the plurality of linear graduation marks being observable through the substantially transparent measurement tube; and
   aligning a respective one of the plurality of linear graduation marks with the proximal end of the measurement tube to provide a respective linear measure of a distance between the distal end of the measurement tube and the cutting member of the retrograde drill disposed in the second position, the respective linear measure corresponding to the thickness of the target material remaining while drilling or after having drilled, in the retrograde fashion, the at least one tunnel or bore through the target material.

13. The method of claim 12 further comprising:
   drilling, in an antegrade fashion by the retrograde drill using the drill bit, at least another tunnel or bore through the target material with the cutting member of the retrograde drill disposed in the first position.

14. The method of claim 12 further comprising:
   positioning the measurement tube so that the distal end thereof makes contact with a surface of the target material while the measurement tube is slidingly engaged over the tubular shaft of the retrograde drill.

15. The method of claim 12 wherein the target material is bone, and wherein the method further comprises:
   measuring, in a ligament surgery procedure by the measurement tube, the thickness of the bone remaining while drilling or after having drilled the at least one tunnel or bore through the bone using the retrograde drill.

\* \* \* \* \*